United States Patent
Andrade et al.

(10) Patent No.: US 11,874,246 B2
(45) Date of Patent: Jan. 16, 2024

(54) POINT-OF CARE DEVICE FOR THE SELECTIVE DETECTION OF POTASSIUM

(71) Applicant: UNIVERSIDAD ROVIRA I VIRGILI (URV), Tarragona (ES)

(72) Inventors: Francisco Javier Andrade, Tarragona (ES); Pascal Blondeau, Tarragona (ES); Marta Novell Recasens, Tarragona (ES); Tomás de Aquino Guinovart Pavón, Tarragona (ES)

(73) Assignee: UNIVERSIDAD ROVIRA I VIRGILI (URV), Tarragona (ES)

( * ) Notice: Subject to any disclaimer, the term of this patent is extended or adjusted under 35 U.S.C. 154(b) by 236 days.

(21) Appl. No.: 17/264,730

(22) PCT Filed: Jul. 31, 2019

(86) PCT No.: PCT/EP2019/070657
§ 371 (c)(1),
(2) Date: Jan. 29, 2021

(87) PCT Pub. No.: WO2020/025688
PCT Pub. Date: Feb. 6, 2020

(65) Prior Publication Data
US 2021/0302351 A1    Sep. 30, 2021

(30) Foreign Application Priority Data
Jul. 31, 2018 (EP) ..................... 18382582

(51) Int. Cl.
*G01N 27/333* (2006.01)
*G01N 27/30* (2006.01)
(Continued)

(52) U.S. Cl.
CPC ....... *G01N 27/301* (2013.01); *G01N 27/3335* (2013.01); *G01N 27/4161* (2013.01);
(Continued)

(58) Field of Classification Search
CPC . G01N 27/301; G01N 27/333; G01N 27/3335
See application file for complete search history.

(56) References Cited

U.S. PATENT DOCUMENTS

| 4,214,968 A | 7/1980 | Battaglia et al. |
| 4,401,548 A * | 8/1983 | Brezinski ............. G01N 27/401 204/420 |

(Continued)

FOREIGN PATENT DOCUMENTS

| CN | 102558724 A | * | 7/2012 | ............... C08K 5/55 |
| GB | 1593269 | * | 7/1981 | ............. G01N 27/30 |

(Continued)

OTHER PUBLICATIONS

Eastman Technical Data Sheet for Butvar® B-98, Feb. 28, 2018, author unknown, downloaded from https://productcatalog.eastman.com/tds/ProdDatasheet.aspx?product=71095422&pn=Butvar+-+B-98 (Year: 2018).*

(Continued)

*Primary Examiner* — Alexander S Noguerola
(74) *Attorney, Agent, or Firm* — SEED INTELLECTUAL PROPERTY LAW GROUP LLP

(57) ABSTRACT

A potentiometric cell capable of selectively measuring potassium comprising an ion-selective working electrode composition prepared from a carrier solvent composition comprising between 1.5 and 2.4 mg of Valinomycin, between 0.4 and 0.6 mg of potassium Tetrakis (4-chlorophenyl) borate (KTFPB), between 52.48 and 78.72 mg of Poly(vinylchloride) (PVC), and between 103.52 and 155.28 mg of Bis(2-ethylhexyl) sebacate (DOS) per ml of the (Continued)

carrier solvent in combination with a specially adapted reference electrode. The cell exhibits improved precision in potassium ion determinations and high selectivity for potassium ions over other cations in a sample specimen such as whole blood or saliva. The electrode compositions exhibits improved properties over a long period of time and therefore has greater shelf life.

10 Claims, 3 Drawing Sheets

(51) Int. Cl.
G01N 27/416 (2006.01)
G01N 33/487 (2006.01)
G01N 33/49 (2006.01)
G01N 33/493 (2006.01)

(52) U.S. Cl.
CPC ....... *G01N 33/48707* (2013.01); *G01N 33/49* (2013.01); *G01N 33/493* (2013.01)

(56) References Cited

U.S. PATENT DOCUMENTS

| | | | | |
|---|---|---|---|---|
| 4,432,366 | A * | 2/1984 | Margules | A61B 5/14542 |
| | | | | 204/414 |
| 4,966,671 | A * | 10/1990 | Nylander | G01N 27/3272 |
| | | | | 205/780.5 |
| 2006/0060471 | A1 | 3/2006 | Murphy et al. | |
| 2011/0056831 | A1* | 3/2011 | Kendig | G01N 27/301 |
| | | | | 204/418 |
| 2018/0028074 | A1 | 2/2018 | Bertsch et al. | |
| 2020/0060541 | A1 | 2/2020 | Andrade et al. | |

FOREIGN PATENT DOCUMENTS

| | | |
|---|---|---|
| JP | 57-17851 A | 1/1982 |
| JP | 57-17852 A | 1/1982 |
| WO | 2016/156941 A1 | 10/2016 |

OTHER PUBLICATIONS

Li et al., "All-solid-sate potassium-selective electrode using graphene as he solid contact," Analyst, 2012, 137, 618 (Year: 2012).*
EPO machine-generated English language translation of Jlnag et al. CN 102558724 A, patent pulished Jul. 11, 2012 (Year: 2012).*
Cheng et al., "All-Solid-State Separted Potassium Electrode Based on SnO2/ITO Glass," Journal of The Electrochemical Society, 154 (11) 1369-1374 (2007) (Year: 2007).*
Chang et al., "Monitoring extracellular K+ flux with a valinomycin-coated silicon nanowire field-effect transistor," Biosensors and Bioelectronics 31 (2012) 137-143 (Year: 2012).*
Hexyl-3-methylimidazolium tris(pentafluoroethyl)trifluorophosphate_ electrode—Google Search Feb. 16, 2023 (Year: 2023).*
Hexyl-3-methylimidazolium tris(pentafluoroethyl) trifluorophosphate _—Google Search Feb. 16, 2023 (Year: 2023).*
1-butyl-3-methylimidazolium bis(trifluoromethane sulfonyl) amide_—Google Search Feb. 16, 2023 (Year: 2023).*
Bakker et al., "Ion-Selective Electrodes Based on Two Competitive Ionophores for Determining Effective Stability Constants of Ion-Carrier Complexes in Solvent Polymeric Membranes," *Anal. Chem.* 70(2):295-302, 1998.
Cuartero et al., "Rubber-based substrates modified with carbon nanotubes inks to build flexible electrochemical sensors," *Analytica Chimica Acta* 827:95-102, 2014.
Guinovart et al., "A reference electrode based on polyvinyl butyral (PVB) polymer for decentralized chemical measurement," *Analytica Chimica Acta* 821:72-80, 2014.
Sjöberg et al., "Paper-based potentiometric ion sensors constructed on ink-jet printed gold electrodes," *Sensors and Actuators B: Chemical* 224:325-332, 2016.

* cited by examiner

POINT-OF-CARE DEVICE FOR THE SELECTIVE DETECTION OF POTASSIUM

FIELD OF THE INVENTION

The present invention pertains to the medical field, particularly to the detection of potassium in clinical samples by using potentiometric sensors. More particularly, the present invention solves the problem of providing devices for measuring potassium, preferably in a single undiluted whole blood drop out of the clinical laboratory.

BACKGROUND OF THE INVENTION

In the diagnosis and treatment of various diseases as well as in preventative health checkups, it is becoming increasingly important to monitor the concentrations of certain ions (e.g. cations) in a patient's body. One cation which has merited considerable attention is potassium. High serum potassium levels are known to cause changes in muscle irritability, respiration and myocardial functions. Low potassium levels can cause excitatory changes in muscle irritability and myocardial function. Therefore, serum potassium determination has become an important diagnostic tool when extremely high or low serum potassium levels are suspected.

One type of ion-selective electrode useful in determining ion concentration in body fluids has an electrode body (usually a glass or plastic container) containing a reference solution in contact with a half-cell of known potential (a reference electrode) and an ion-selective membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the membrane. This type of electrode is referred to in the art as a "barrel" electrode.

The ion-selective membranes in barrel electrodes may be comprised of glass, solid salt precipitates or polymers. The polymeric membranes generally comprise a polymeric binder or support as the supporting matrix which is impregnated with a solution of an ion-selective carrier in a carrier solvent. The ion-selective carrier is a compound which is capable of sequentially complexing the desired ion and transporting the ion across the membrane-solution interface. This compound is also referred to in the art as an "ionophore" or "ion carrier". Depending upon the ionophore, solvent and binder, membranes of this type can be used to detect a particular ion preferentially to other ions which may be in the solution.

Carrier solvents useful in ion-selective membranes must exhibit certain properties. The carrier solvents must provide suitable ion mobility in the membranes, be compatible with the supporting matrix and be sufficiently hydrophilic to permit rapid wetting of the membrane by aqueous solutions but sufficiently water-insoluble to inhibit leaching out into those aqueous solutions. Ideally, they also plasticize the supporting matrix and are substantially nonvolatile, thereby providing extended shelf life for the membrane.

A significant advance in the ion-selective-electrode art is the dry-operative electrode described in U.S. Pat. No. 4,214,968 (issued Jul. 29, 1980 to Battaglia et al). Prior to the discovery of such dry-operative ion-selective electrodes, electrodes had to be either stored in an aqueous solution or treated with aqueous solution just prior to use in an ion-activity-determining operation. The term "dry-operative" refers to an ion-selective electrode which provides reproducible potentiometric determination of ion activity which is related to the ion concentration of an aqueous test solution with no requirement for wet storage or preconditioning prior to use.

One of the specific ion-selective electrodes disclosed in the examples of Battaglia et al is a potassium ion-selective electrode using valinomycin as the potassium-selective ionophore dissolved in a variety of solvating compounds. Among useful solvents mentioned are phthalates, sebacates, aromatic and aliphatic ethers, phosphates, mixed aromatic aliphatic phosphates, adipates and mixtures thereof. In the potassium-selective electrodes utilizing valinomycin as the ionophore, particularly preferred carrier solvents disclosed are bromophenyl phenyl ether and certain trimellitates.

Dry-operative ion-selective electrodes are also described in Fuji's Japanese Patent Publication Nos. 17851/1982 and 17852/1982, both published Jan. 29, 1982. In the first example of each publication, a $K^+$-selective electrode containing valinomycin, poly(vinyl chloride) and dioctyl phthalate as the carrier solvent. However, it has been observed that an electrode prepared using dioctyl phthalate as the carrier solvent exhibited poor precision in potassium ion determinations under certain conditions of use.

Further, it has been found that potassium ion-selective membranes and electrodes containing the membranes which are prepared according to the teaching of the Battaglia et al patent using the preferred carrier solvents taught therein (e.g. triisodecyl trimellitate), also exhibit undesirably poor precision in potassium ion determinations under certain conditions of use. It has also been observed that such membranes and electrodes are often sensitive to ambient temperature fluctuations thereby worsening precision in assay results. This poor precision worsens with extended storage.

On the other hand, blood potassium concentration is closely regulated by the body maintaining the potassium levels between 3.5 to 5.5 mM. However, potassium disorders are common, and severe cases can have fatal consequences. Potassium concentrations lower than 3.5 mM are known as hypokalemia and higher than 5.5 mM as hyperkalemia, and both conditions can lead to arrhythmias or a cardiac arrest in extreme conditions. 10% of the patients taking angiotensin-converting enzyme (ACE) inhibitor or angiotensin receptor blocker (ARB) used for the treatment of hypertension and congestive heart failure might develop hyperkalemia. Moreover, these drugs are therapeutically indicated for patients with renal insufficiency and diabetes which are at higher risk because of the inherent complications of their diseases. 27% of deaths in patients requiring hemodialysis are caused by arrhythmic problems. Although it is proven that continuous monitoring of potassium levels on these patients reduce their risk of suffering hyperkalemia, this is not a common practice and it depends mainly on the healthcare structure Immediate potassium measurements, as well as continuous monitoring of potassium, may therefore contribute to improve patients care. Such issues may be covered by point-of-care devices (POC) which potential interest grows exponentially over the last decade. First, POC are particularly relevant when the turnaround time to get the result is crucial for the medical decision. Second and most importantly, POC overcome the problem of centralization of clinical analysis, i.e. for measurements outside the medical facilities either by the same patients (homecare) or by the medical professionals in situations such as emergency home visits, doctor's offices in remote areas, etc. Measuring potassium in such conditions may be very useful in emergency facilities to discard life-threatening conditions for patient suffering from chronic kidney disease (CKD) and cardiovascular diseases. In addition, potassium-POC could not only be beneficial for acute conditions but also for managing chronic diseases, where the continuous monitoring of biomarkers may help to prevent critical situations by giving relevant insights to the doctors to support clinical decisions. In this way, several studies revealed that abnormal potassium values are connected to higher mortality.

Several POC devices for measuring biomarkers including potassium are in the market, however, as far as we know, there are no POC devices which required a volume of a biological sample of less than 90 microliters capable of measuring potassium in a single whole blood drop out of the clinical laboratory.

Thus, the objective of this invention is to provide a POC by comparison with the reference technique used in the central laboratory of a hospital, capable of measuring potassium, by using a small volume of a single whole blood drop out of the clinical laboratory.

BRIEF DESCRIPTION OF THE INVENTION

In accordance with this invention, it has been found that certain ion-selective compositions exhibit high selectivity for potassium ions over other cations in a sample specimen such as whole blood, sweat or saliva as well as unexpected improved precision in potassium ion determinations. In particular, it has been found that ion-selective compositions or membranes comprising (ISM) between 1.5 and 2.4 mg of Valinomycin, between 0.4 and 0.6 mg of potassium Tetrakis (4-chlorophenyl) borate (KTFPB), between 52.48 and 78.72 mg of Poly(vinylchloride) (PVC), and between 103.52 and 155.28 mg of Bis(2-ethylhexyl) sebacate (DOS) dissolved in a carrier solvent such as 1 mL of THF (Tetrahydrofuran), exhibit improved precision in potassium ion determinations. Further, these compositions exhibit these improved properties over a long period of time and therefore have greater shelf life.

DESCRIPTION

The present invention solves the problem of providing devices for measuring potassium, preferably in a single undiluted whole blood drop out of the clinical laboratory.

In particular, a first aspect of the present invention provides for a potassium ion-selective membrane (ISM) comprising a composition which in turn comprises between 1.5 and 2.4 mg of Valinomycin, between 0.4 and 0.6 mg of potassium, lithium, ammonium or cessium Tetrakis (4-chlorophenyl) borate, between 52.48 and 78.72 mg of Poly (vinylchloride) (PVC), preferably such PVC has a molecular weight between 50000-250000 g/mol, more preferably between 70000-150000 g/mol, and between 103.52 and 155.28 mg of Bis(2-ethylhexyl) sebacate (DOS), (from hereinafter this composition shall be referred to as "PVC 2") dissolved in a suitable carrier solvent such as 1 mL of THF (Tetrahydrofuran) or in any organic solvent capable of dissolving these components such as DMF. As shown in the examples (see example 1, preferably section 1.2 of example 1) such PVC 2 composition dissolved in a suitable carrier exhibited improved precision in potassium ion determinations. Further, this composition exhibited such improved properties over a long period of time and had an extended shelf life.

It is herein noted, that all of the above mentioned quantitative references of each of the components of the PVC 2 composition are expressed in weight per 1 ml of carrier solvent.

Preferably, the potassium ion-selective membrane (ISM) comprises or consists of between 1.8 and 2.2 mg/ml of Valinomycin, between 0.45 and 0.55 mg/ml of potassium, lithium, ammonium or cessium Tetrakis (4-chlorophenyl) borate, between 59.04 and 72.16 mg/ml of Poly(vinylchloride) (PVC), preferably such PVC has a molecular weight between 50000-250000 g/mol, and between 116.46 and 142.34 mg/ml of Bis(2-ethylhexyl) sebacate (DOS), dissolved in a suitable carrier solvent such as THF (Tetrahydrofuran).

Figure 5:
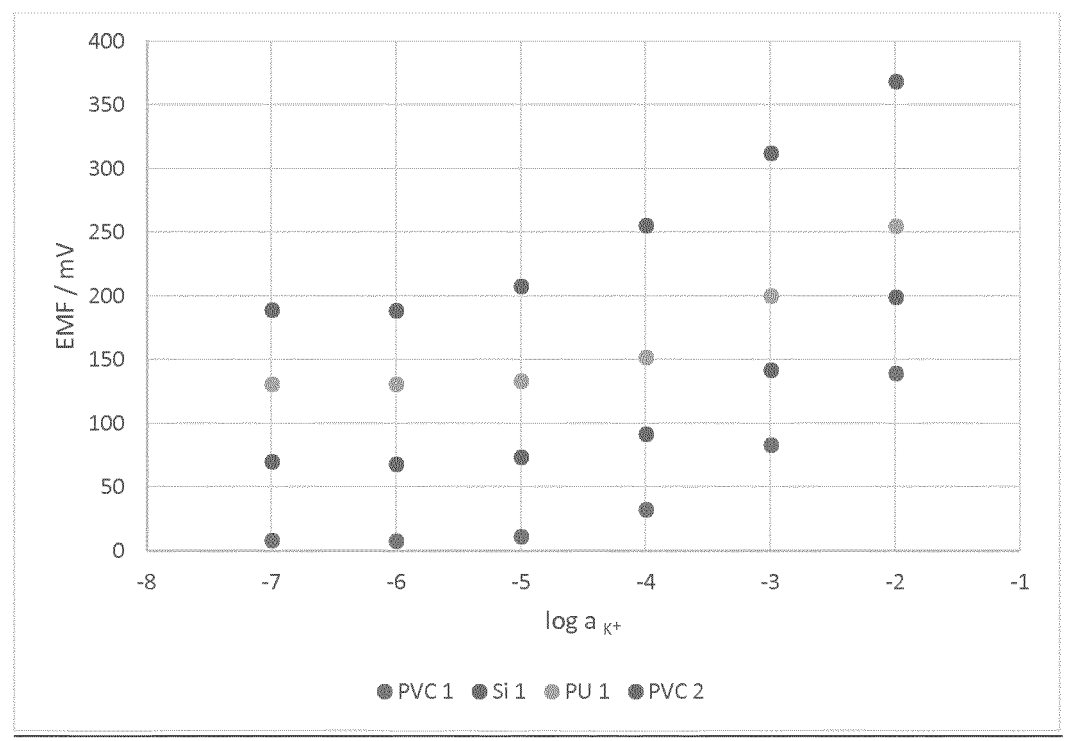
FIG. 5. Corresponding calibration curves to the above time traces

It is noted that an ion-selective membrane comprising composition PVC 2 can be formed by incorporating the carrier solvent and each of the components of PVC 2 as described in example 1. In addition, a working electrode of a device capable of selectively measuring potassium can be prepared by using the above mentioned ion-selective membrane; namely, for this purpose, a conductive material such as carbon-ink, silver, Zinc or gold, or any other material that is capable of transducing the potentiometric signal, can be deposited on one side of a substrate, such as, but not limited to, paper or filter paper, plastic, rubber, textile or carbon filter, to create a conductive surface. Such treated substrate, such as paper, can be then cut into strips or into any other geometrical shape. To build the electrodes, the conductive substrate strips can be sandwiched within two masks. The top mask should have a, preferably circular, window to expose the electroactive surface, where the corresponding membrane can be drop cast (see FIG. 5).

Therefore, in a preferred embodiment of the first aspect, the invention refers to a working electrode, that preferably forms part of a device capable of selectively measuring potassium, that comprises an ion-selective membrane comprising composition PVC 2 dissolved in a suitable carrier solvent such as those referred to hereinabove.

In addition, in a second aspect, the present invention provides for a reference membrane comprising a composition which in turn comprises between 8 and 12 mg of sodium chloride, preferably between 9 and 11 mg of sodium chloride, more preferably about 10 mg of sodium chloride, and between 94.88 mg and 142. 32 mg of Butvar B-98, preferably between 106.74 mg and 130.46 mg of Butvar B-98, still more preferably about 118.6 mg of Butvar B-98 (PVB) (from hereinafter this composition shall be referred to as "PVB2"), dissolved in an appropriate solvent such as 1 mL of methanol. This cocktail can be stored at ambient temperature and will remain stable for more than 2 months. It is noted that PVB or Butvar B-98 is understood as polyvinyl butyryl having a molecular weight between 40000-70000 g/mol with butyryl content between 78 and 80% weight per total weight of the polyvinyl butyryl (w/w), hydroxyl content between 18 and 20% (w/w) and acetate less than 2.5%, preferably between 1.5 and 2.5% (w/w).

It is herein noted, that all of the above mentioned quantitative references of each of the components of the PVB2 composition are expressed in weight per 1 ml of carrier solvent.

Such reference membrane composition can be formed by incorporating the carrier solvent and each of the above mentioned components as described in example 1. In particular, for the reference electrode of the potassium sensor to be prepared, a conductive material such as Ag/AgCl ink, preferably cured for about 10 minutes at about 90° C., can be deposited on one side of a substrate, such as paper or filter paper, plastic, rubber, textile or carbon filter, to create a conductive surface. Such treated substrate, such as paper, can be then cut into strips or into any other geometrical shape. To build the electrode, the conductive substrate strips can be sandwiched within two masks. The top mask has a circular window to expose the electroactive surface, where the corresponding membrane can be drop cast (see FIG. 5).

Therefore, in a preferred embodiment of the second aspect, the invention refers to a reference electrode, that preferably forms part of a device capable of selectively measuring potassium, comprising composition PVB2 dissolved in a suitable carrier solvent such as referred to hereinabove.

The membrane compositions useful in this invention preferably have a glass transition temperature (Tg) of greater than about −50° C. in order to have desired film characteristics. Tg can be determined by any convenient method suitable for this purpose. For example, one such method is differential scanning calorimetry, as described in Techniques and Methods of Polymer Evaluation, Vol. 2, Marcel Dekker, Inc., N.Y. 1970. Preferably, the membranes have a Tg in the range of from about −50 to about −20° C.

The membranes useful in the present invention contain the described components over the specific range of concentrations or coverages specified above or below. The carrier solvent should be present in an amount sufficient to solvate the membrane compositions. The amount therefore depends on the particular solvent chosen. Generally, more solvent is used than is necessary to solvate the ion-selective membrane so that it remains solvated under a variety of storage conditions.

In addition to the membrane compositions, and carrier solvents, the described membrane compositions optionally contain other components such as surfactants and plasticizers in amounts known to those skilled in the art. As noted, surfactants are useful components of the described membranes. The surfactants serve a variety of functions including improving the coatability of the membrane composition and improving the solvation of valinomycin by the binder or carrier solvent. Useful surfactants include nonionic surfactants such as the alkylaryl polyether alcohols (Tritons™) available from Rohm and Haas Co; (p-isononylphenoxy)-polyglycidol (Surfactant 10G™) available from Olin Mathieson Corp; polyoxyethylene (20) oleyl ether (Brij 98™), polyoxyethylene sorbitan monolaurate (Tween 20™) and Span 80™, all available from Atlas Chemical Industries; poly(dimethyl-comethylphenyl siloxane) (DC-510™) available from Dow Corning; Zonyl FSN™ available from E. I. duPont; and fluorochemical surfactant FC134™ available from 3M Co.

It is noted that, as described in the examples of the present specification, comparison between the reference electrode PVB2 with a conventional reference electrode (PVB1) for the detection of potassium, provides for an experimental reproducibility of 100%, which compared with the reproducibility obtained of 30% achieved with the electrode composition (PVB1), constitutes a considerable success.

|  | PVB 1 | PVB 2 |
|---|---|---|
| NaCl | 50 mg | 10 mg |
| PVB | 78 mg | 118 mg |
| Methanol | 1 mL | 1 mL |
| Response to K | 0 mV | 0 mV |
| Response to Alb | 0 mV | 0 mV |
| Stabilization time | 18 h | 18 h |
| Sensitivity in combination with K electrode |  | 55.4 ± 0.3 mV/dec |

The key factor to improve the electrode construction reproducibility of PVB2 was the dispersion of sodium chloride in the polymeric matrix composed of PVB in methanol. In this way, the composition was optimized in 10 fold to reach a suitable dispersion which was stable in time. For this, the amount of salts was significantly reduced five-fold whereas the polymer amount was multiplied by 1.5 in comparison to the composition of PVB1. The former, is of particular interest so that the deposition of the reference membrane cocktail could be performed by conventional methods such as drop casting, or spin coating, in a way in which the electrode could be prepared in an automatized manner. It is, however, noted that further reference membranes different from composition PVB2 can also be used in combination with the ion-selective membrane of the invention, PCV 2, providing an improved potentiometric cell. In this sense, such further reference membranes are required to be capable of having ionic conduction, based on either solid salts such as sodium chloride or liquid salts such as ionic liquids, entrapped in a polymeric matrix, either PVB, PVC with or without a plasticizer. The resulting component can be dissolved in suitable organic solvents such as THF or Methanol.

Ideally, the further reference membranes should not provide a response to any of the species that are contained in the tested sample to measure but should preferably provide an immediate stabilization time. Therefore, when measuring in blood, an important parameter to be considered is the response of the sensor to proteins such as albumin, such response should be as low as possible.

The reference membranes useful in the present inventions should thus not display response to ions but show stabilization time in different orders of magnitude (from a few seconds to hours), and different responses to albumin. Depending on the application, one may select the more suitable membrane to fit the analytical requirements.

For measuring potassium, preferably in a single undiluted whole blood drop out of the clinical laboratory, reference membranes such as PVC 3 and PVC 4 (see table below) are particularly preferred since such membranes show an immediate stabilization time in comparison to PVB 3 and PVB 4 (see table below), while they show almost no response to albumin in comparison to reference membranes such as PVC 1.

|  | PVB 3 | PVB 4 | PVC 0 | PVC 3 | PVC 4 |
|---|---|---|---|---|---|
| Composition | 80 mg PVB | 29 mg PVB | 29 mg PVC | 27 mg PVC | 53 mg PVC |
|  | 57 mg IL 1 | 59 mg Plasticizer DOS | 59 mg Plasticizer DOS | 53 mg IL 2 | 27 mg IL 2 |
|  | 1 mL Methanol | | | 1 mL THF | 1 mL THF |
|  | | 38 mg IL 1 | 38 mg IL 1 | | |
|  | | 1 mL THF | 1 mL THF | | |
| Response to K | 0 mV | 0 mV | 1 mV | 0.5 ± 0.7 mV | 0.1 ± 0.3 mV |
| Response to Albumin | 0 mV | 20 ± 10 mV | 40 ± 10 mV | 0.1 ± 0.2 mV | 0.4 ± 0.1 mV |
| Stabilization time | 1000 s | 200 s | 0 s | 50 s | 30 s |
| Sensitivity in combination with K electrode | n.d. | n.d. | n.d. | 55.6 ± 0.1 mV/dec | 55.2 ± 2.3 mV/dec |

Note:
Response to K: total change of the reference electrode from 0 to 0.01M of potassium ion; response to Albumin: total change of the reference electrode from 0 to 50 g/L of Albumin; n.d.: not determined.

It is noted that, in this context, "PVC" is understood as a poly(vinyl chloride) having a molecular weight between 22000-233000 g/mol.

In this context, a "plasticizer" is any liquid added to the membrane to make it softer and more flexible. Optimum plasticizers allow for the membrane to have optimum physical properties and ensures relatively high mobilities of their constituents. Examples of plasticizers are exemplified herein below:

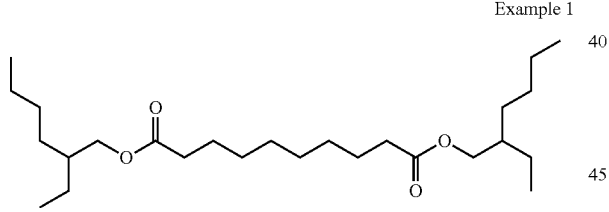

Example 1

DOS or Bis(2-ethylhexyl) sebacate

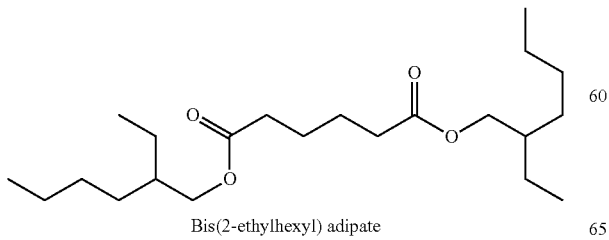

Example 2

Bis(2-ethylhexyl) adipate

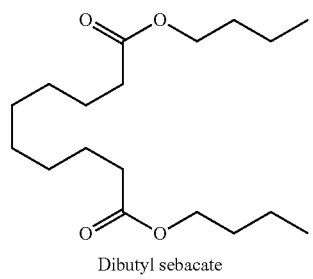

Example 3

Dibutyl sebacate

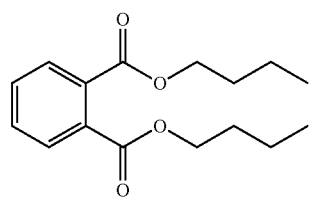

Example 4

Dibutyl phthalate

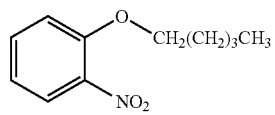

Example 5: 2-Nitrophenyl pentyl ether

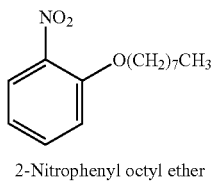

2-Nitrophenyl octyl ether

In the context of the present invention, "IL" is understood as any ionic liquid, preferably an imidazolium substituted with alkyl chains in positions 1 and 3. Being R1 any alkyl between 1 to 3 carbons, and R2 between 2 to 12 carbons, with any lipophilic counter anion.

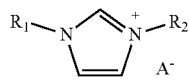

R₁: $C_1$-$C_3$
R₂: $C_2$-$C_{12}$
A⁻: Lipophilic counter anion
IL1 is: 1-Hexyl-3-methylimidazolium tris(pentafluoroethyl)trifluorophosphate

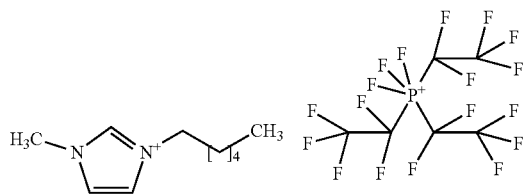

IL2: 1-butyl-3-methylimidazolium bis(trifluoromethane sulfonyl)amide

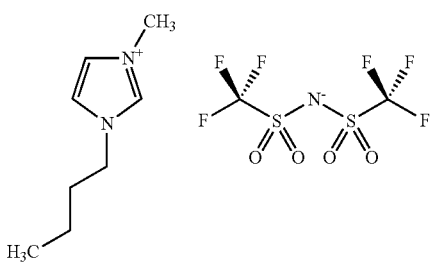

Therefore, in another preferred embodiment of the second aspect, the invention refers to a reference electrode, that preferably forms part of a device capable of selectively measuring potassium, comprising between 20 and 60 mg of 1-butyl-3-methylimidazolium bis(trifluoromethane sulfonyl)amide, and between 20 mg and 60 mg of poly(vinyl chloride) having a molecular weight between 22.000-23.3000 g/mol, dissolved in an appropriate solvent such as 1 mL of THF (Tetrahydrofuran), wherein the device preferably further comprises an ion-selective membrane comprising composition PVC 2 dissolved in a suitable solvent as described hereinabove. Preferably, such device is a potentiometric cell capable of selectively measuring potassium.

In another preferred embodiment of the second aspect, the invention refers to a reference electrode, that preferably forms part of a device capable of selectively measuring potassium, comprising between 8 and 12 mg of sodium chloride, and between 94.88 mg and 142.32 mg of Butvar B-98, dissolved in an appropriate solvent such as 1 mL of methanol, wherein the device preferably further comprises an ion-selective membrane comprising composition PVC 2 dissolved in a suitable solvent as described hereinabove. Preferably, such device is a potentiometric cell capable of selectively measuring potassium.

In another preferred embodiment of the second aspect, the invention refers to a reference electrode, that preferably forms part of a device capable of selectively measuring potassium, comprising between 9 and 11 mg of sodium chloride, and between 106.74 mg and 130.46 mg of Butvar B-98, dissolved in an appropriate solvent such as 1 mL of methanol, wherein the device preferably further comprises an ion-selective membrane comprising composition PVC 2 dissolved in a suitable solvent as described hereinabove. Preferably, such device is a potentiometric cell capable of selectively measuring potassium.

In another preferred embodiment of the second aspect, the invention refers to a reference electrode, that preferably forms part of a device capable of selectively measuring potassium, comprising between 20 and 90 mg of Bis(2-ethylhexyl) sebacate) (DOS), between 20 mg and 110 mg of Butvar B-98, and between 20 mg and 90 mg of 1-Hexyl-3-methylimidazolium tris(pentafluoroethyl)trifluorophosphate dissolved in an appropriate solvent such as 1 mL of THF (Tetrahydrofuran), wherein the device preferably further comprises an ion-selective membrane comprising composition PVC 2 dissolved in a suitable solvent as described hereinabove. Preferably, such device is a potentiometric cell capable of selectively measuring potassium.

In another preferred embodiment of the second aspect, the invention refers to a reference electrode, that preferably forms part of a device capable of selectively measuring potassium, comprising between 25 and 30 mg of 1-butyl-3-methylimidazolium bis(trifluoromethane sulfonyl)amide, and between 50 mg and 60 mg of poly(vinyl chloride) having a molecular weight between 22.000-23.3000 g/mol, dissolved in an appropriate solvent such as 1 mL of THF (Tetrahydrofuran), wherein the device preferably further comprises an ion-selective membrane comprising composition PVC 2 dissolved in a suitable solvent as described hereinabove. Preferably, such device is a potentiometric cell capable of selectively measuring potassium.

In another preferred embodiment of the second aspect, the invention refers to a reference electrode, that preferably forms part of a device capable of selectively measuring potassium, comprising between 50 and 60 mg of 1-butyl-3-methylimidazolium bis(trifluoromethane sulfonyl)amide, and between 25 mg and 30 mg of poly(vinyl chloride) having a molecular weight between 22.000-23.3000 g/mol, dissolved in an appropriate solvent such as 1 mL of THF (Tetrahydrofuran), wherein the device preferably further comprises an ion-selective membrane comprising composition PVC 2 dissolved in a suitable solvent as described hereinabove. Preferably, such device is a potentiometric cell capable of selectively measuring potassium.

In another preferred embodiment of the second aspect, the invention refers to a reference electrode, that preferably forms part of a device capable of selectively measuring potassium, comprising between 55 and 65 mg of Bis(2-ethylhexyl) sebacate) (DOS), between 25 mg and 35 mg of Butvar B-98, and between 35 mg and 45 mg of 1-Hexyl-3-methylimidazolium tris(pentafluoroethyl)trifluorophosphate dissolved in an appropriate solvent such as 1 mL of THF (Tetrahydrofuran), wherein the device preferably further comprises an ion-selective membrane comprising composition PVC 2 dissolved in a suitable solvent as described hereinabove. Preferably, such device is a potentiometric cell capable of selectively measuring potassium.

On the basis of the above, a further aspect of the invention, a third aspect, refers to a device, preferably a POC device, capable of measuring potassium, preferably in a single whole blood drop out of the clinical laboratory, made by combining any of the above mentioned reference membranes (reference is made to the second aspect of the invention or to any of its preferred embodiments) and the ion-selective membrane described in the first aspect of the invention, PVC 2, thus resulting in a whole potentiometric cell. Preferably such whole potentiometric cell is connected to an instrument for EMF reading and the data read through a tablet with the suitable software interface.

In a particularly preferred embodiment, the described membranes are used to provide a potassium ion-selective electrode or potentiometric cell comprising:
 (a) a reference element comprising a, preferably dried residue, of composition PVB2, or of any of the above mentioned further reference membranes (reference is made to the second aspect of the invention or any of its preferred embodiments), in a suitable solvent and,
 (b) in contact, through the sample for analysis, so that in this manner such sample closes the potentiometric circuit, with the reference element, an ion-selective membrane of preferably predetermined uniform thickness in regions thereof intended for physical contact with the sample for analysis, the membrane comprising composition PVC 2 dissolved in a suitable solvent as described hereinabove.

As already mentioned, in a fourth aspect, the electrodes of this invention can be used to determine the concentration of potassium in an aqueous solution, e.g. biological fluids such as whole blood, preferably undiluted whole blood, intracellular fluids, blood sera, blood plasma, sweat and urine. Generally, a portion of the solution to be assayed is brought into contact with the ion-selective electrode described hereinabove which is capable of making potentiometric measurements related to the potassium ion concentration. Subsequently, the difference in potential between the portion of aqueous solution and the reference electrode is measured. Preferably, a drop of the aqueous solution is spotted onto the potassium ion-selective membrane of such electrode with a pipette or other suitable means, but other ways of contacting the electrode with the solution are acceptable.

Figure 2:
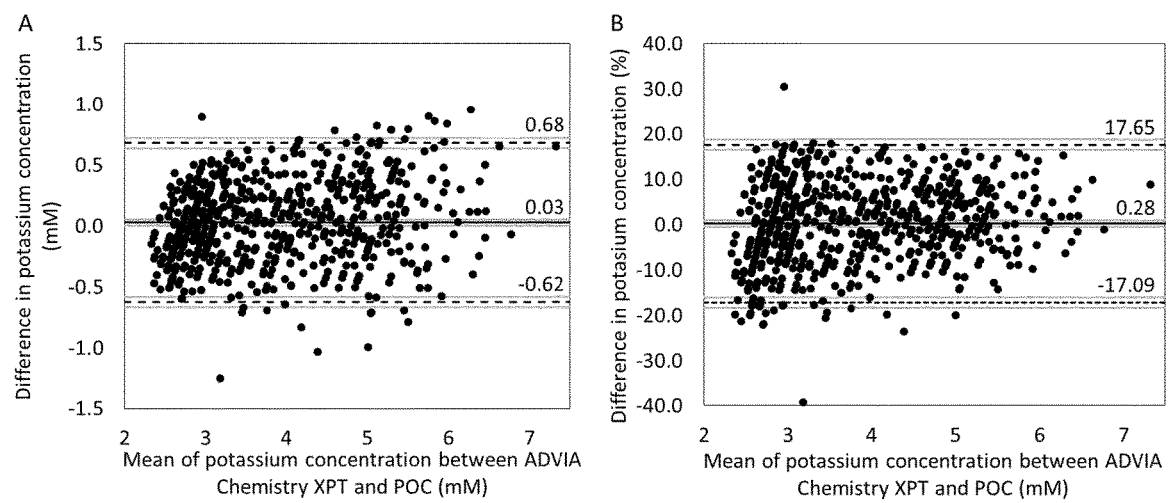
FIG. 2. Comparison of potassium values between the reference technique and the developed potassium sensor by Bland-Altman plots displayed in difference in mM (A) and percentage (B). The solid line is the average difference, the dashed lines the limits of agreement, and the grey lines the 95% CIs.

In addition, the authors of the present invention validated the performance of a POC device capable of measuring potassium as described in the third aspect in undiluted whole blood samples. To do so, the correlation of the results obtained by the POC were compared to the results obtained by the ADVIA Chemistry XPT system. Passing-Bablock regression and Blant-Altman analysis confirmed that there is a strong correlation between the results obtained by both methodologies with a small bias and limits of agreement in −0.62 and 0.68 mM (FIG. 2A). Whether the bias and limits of agreement are suitable or not, it is therefore a clinical question and not a statistical one. As normal potassium levels in blood can vary from 3.5 to 5.5 mM a bias of 0.03 mM appeared as insignificant. Moreover, the confidence intervals obtained by the POC (−0.62/0.68 mM) are suitable for the type of situations where a POC will be used—such as screening for general conditions in the global population or control and monitoring of chronic patients. With the general B&A analysis, it could be concluded that there is not a clear trend between the difference within the methodologies and the concentration (FIG. 2B).

The higher contribution to the variability of the technique comes from the precision of the sensor (0.25 mM). Other parameters such as the manual calibration or some interferences from blood may contribute to the remaining variability. The main issue that affects the potassium measurements in blood is the hemolysis of the sample, i.e. as the erythrocytes are broken, their intracellular components are released into the blood and as the intracellular potassium concentration is highly superior to the plasmatic one, this leads to misleading results (highly elevated concentration). As the samples where measured first with the ADVIA Chemistry XPT system in plasma and later homogenized and measured in blood with the POC, some of the abnormal higher potassium values could be coming from some grade of hemolysis of the blood. Another parameter that has to be considered is that the ADVIA Chemistry XPT system measures with indirect ion selective electrodes in a pre-diluted sample, while the POC device measures with direct ISEs in whole blood. Lipemia in serum causes a reduction in the aqueous fraction leading to abnormal lower values, which does not happen in the whole blood measurements. This may be an additional source of variation between the two methodologies. Since the overall results highly correlate with the reference technique, it was concluded that the possible interferences were not affecting significantly the results here.

Once validated the measurement, the advantages and limitations of the POC versus a reference technique must be considered. This point-of-care device is not conceived to compete with the reference technique in the healthcare facility, but rather to complement the conventional analysis by giving an immediate response when required. Although the value is less precise, it may have a great impact when discarding life-threatening conditions. Hence, some of the classical parameters may have less importance than other ones. In this way, conventional parameters such as sensitivity, limit of detection and linear range are comparable in both techniques. Precision for the POC is good enough for the situations for which is intended to be used. In the same way, the cost per analysis may be higher with the POC device in the first step, but, as mentioned previously, the immediate response may reduce strongly indirect related costs. It may have huge impact on the early detection of several medical conditions that will avoid future problems and complications in the patient health, eventually reducing the costs of the treatment.

The POC meets the requirement for direct analysis since it uses a small amount of blood and that no pre-treatment is performed. The POC presents the benefits that this implies, especially the reduction of the time between the sample withdraw from the patient and the given result. This POC has the particular advantage to work with paper-based sensors, which are extremely cheap and suitable for scaling production. No contamination neither fouling of the membrane are observed in such conditions.

This invention thus clearly illustrates the usefulness of the POC devices according to the third aspect of the invention in a real scenario (outside the laboratory), validating the potassium measurements in comparison with a reference technique. Consequently, the point-of-care potassium device of the present invention has demonstrated an excellent correlation with the reference method for patients on dialysis, showing that there is a strong correlation between the point-of-care (POC) device and the reference method ($R^2$=0.968). Bland-Altman analysis shows no bias between the two methods and revels that 95.5% confidence intervals are between −0.62 to 0.68 mM. No significant interferences have been detected due to the measurement of potassium in total blood compared to its conventional measurement in serum.

The following examples are merely presented to illustrate the practice of this invention.

EXAMPLES

Example 1. Point-of Care Device for the Detection of Potassium in Blood of Patients on Hemodialysis 1. Material & Methods Whatman® Grade 5 qualitative filter paper was used for the fabrication of the electrodes. All chemicals were purchased from Sigma-Aldrich. All solutions were prepared using 18.2 MΩ cm$^{-1}$ double deionized water (Milli-Q water systems, Merck Millipore). Butvar B-98 (PVB) was obtained from Quimidroga S.A. (Barcelona, Spain). Plastic mask (Arcare 8565) were provided by Adhesives Research Inc., Limerick, Ireland. Carbon-ink and Silver/silver chloride (Ag/AgCl) ink was purchased from Creative Materials Inc. (Massachusetts, USA).

Electrode Geometry

As a first step, the preparation of the paper used as a substrate was performed. For the working electrodes, a carbon-ink was deposited on one side of the filter paper to create a conductive, surface. For the reference electrode, a filter paper was first painted with a conductive Ag/AgCl ink and cured for 10 minutes at 90° C.

These treated papers were then cut into 10×5 mm strips. To build the electrodes, the conductive paper strips were sandwiched within two plastic masks. The top mask has a circular window of 3 mm diameter to expose the electroactive surface, where the corresponding membrane (either for the working or for the reference) was drop cast (see FIG. 5)

Working Electrode Composition (PVC 2):

A potassium ion selective membrane (ISM) (from hereinafter PVC 2) containing 2 mg of Valinomycin, 0.5 mg of potassium Tetrakis (4-chlorophenyl) borate (KTFPB), 65.6 mg of Poly(vinylchloride) (PVC), and 129.4 mg of Bis(2-ethylhexyl) sebacate (DOS) was dissolved in 1 mL of THF. The cocktail was then stored at 4° C. and remained stable for more than 2 weeks.

Reference Electrode Composition (PVB2):

The reference membrane (from hereinafter PVB2) contained 10 mg of sodium chloride and 118.6 mg of Butvar B-98 (PVB). The membrane was prepared by dissolving the components in 1 mL of methanol. The cocktail was stored at ambient temperature and remained stable for more than 2 months.

Figure 3:
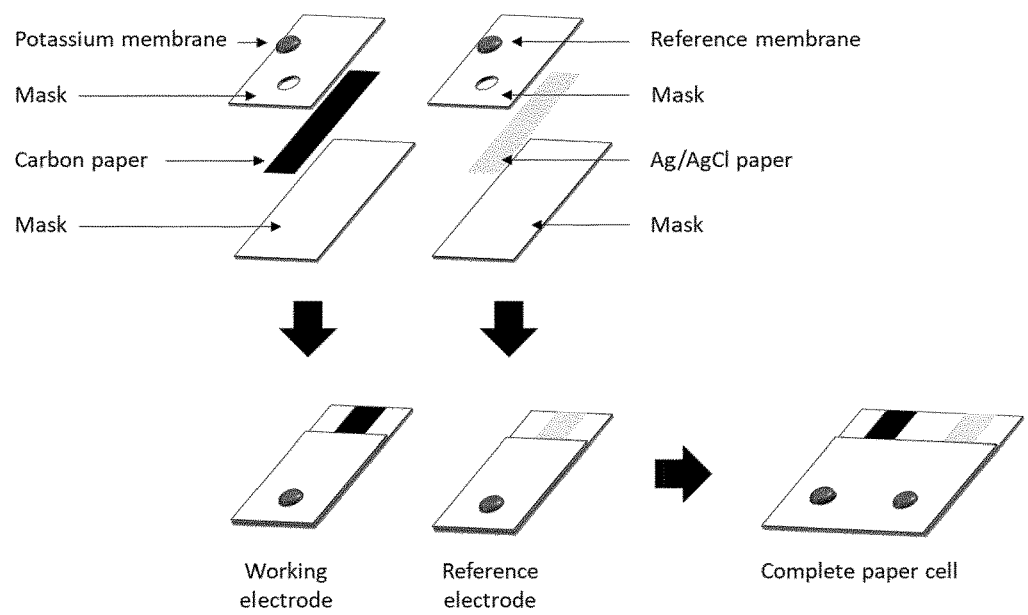
FIG. 3. Construction of paper-based sensors: the working and the reference electrode as well as the complete potentiometric cell.

Deposition of the Cocktail:

Potassium electrodes were prepared by drop-casting 15 μL of the membrane (in 3 drops of 5 μL, waiting for 2 minutes between each drop) in an orifice of 3 mm (see FIG. 3).

Reference electrodes were prepared by depositing 5 mg of sodium chloride in the orifice (3 mm) and then drop-casting 30 μL of the reference membrane (in 3 consecutive drops of 10 μL, waiting for 5 minutes between each drop) (see FIG. 3).

Conditioning of the Electrodes

Reference electrode: 18 hours in a KC10.01 M before use.

Working electrode: no conditioning was required

Figure 4:
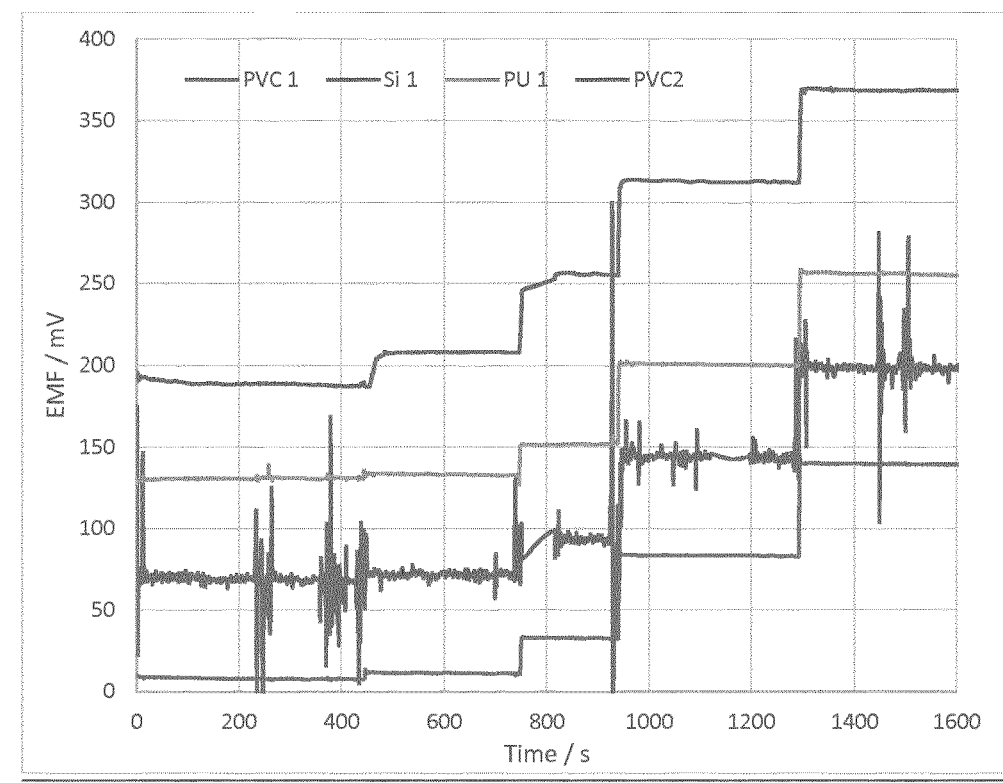
FIG. 4. Time trace corresponding to Si, PU, PVC 1 and PVC 2 in artificial serum

2. Comparison Between Working Electrode as Described Above (See Materials and Methods) with Conventional Working Electrodes for the Detection of Potassium Conventional working electrodes for potassium detection have been reported as Si, PU and PVC 1, where Si, Pu and PVC1 states for Silicon rubber, Polyurethane and Polyvinylchloride polymer respectively (please refer to the table below for the precise composition of each of these electrodes). However, Si has the disadvantage of displaying substantial instrumental noise in the time trace so that additional signal treatment would be necessary for the use of this membrane in real whole blood samples (see FIG. 4). Si-based electrodes were therefore discarded for measuring potassium in a single whole blood drop out of a clinical laboratory.

|  | PVC 1 | Si | PU | PCV2 |
|---|---|---|---|---|
| Compositon | 2 mg Ionophore I<br>0.5 mg KTChPB<br>64.7 mg DOS<br>32.8 mg PVC | 2.5 mg Ionophore I<br>97.5 mg Silicone rubber | 2 mg Ionophore I<br>0.5 mg KTChPB<br>64.7 mg DOS<br>32.8 mg PU | 2 mg Ionophore I<br>0.5 mg KTChPB<br>129.4 mg DOS<br>65.6 mg PVC |

Pu-based sensors have relatively good performance in water (see figures) although this performance is drastically reduced when artificial serum is used. In fact, two orders of magnitude are lost in the linear range when artificial serum is used instead of water (from −6 (mM) to −2 (mM) and from −4 (mM) to −2 (mM) for water and artificial serum respectively). In addition, the Limit of detection for Pu-based sensors is decreased from −6.5 (log [K$^+$]/M) down to −5 (log [K$^+$]/M) as well as the sensitivity from 57.2 down to 53.2 mv/dec when artificial serum is used instead of water. For these reasons, the PU-based electrodes were also discarded for measuring potassium in a single undiluted whole blood drop out of a clinical laboratory since such Limits of detection are insufficient for reliably detecting potassium in undiluted whole blood.

In addition, PVC 1 also suffers a drastic reduction of performance from water to artificial serum measurements (two orders of magnitude less, a LOD decrease to −4.5 (log [K$^+$]/M) and a sensitivity down to 54 mv/dec). PVC 1 was also thus discarded for whole blood detection (see figures).

However, PVC 2 composition allows detecting potassium in artificial serum with better performance (see figures). The Sensitivity is the highest reported of the tested sensors (55.7 mV/dec in artificial serum). The linear range is only reduced by one order of magnitude (which is sufficient for the targeted application) with a limit of detection of −5.6 (log [K$^+$]/M). Therefore, working electrode composition PVC 2 provides a substantial improvement over known working electrode compositions for undiluted whole blood measurement.

3. Comparison Between the Reference Electrode PVB2 with a Conventional Reference Electrode for the Detection of Potassium The reference electrode composition described in the materials and methods above-mentioned containing sodium chloride (NaCl) and polymer (polyvinylButyral, PVB) provided for an experimental reproducibility of 100%, which compared with the reproducibility obtained of 30% achieved with a previously reported electrode composition (PVB1), constitutes a considerable success.

|  | PVB 1 | PVB 2 |
| --- | --- | --- |
| NaCl | 50 mg | 10 mg |
| Butvar-95 | 78 mg | 118.6 mg |
| Methanol | 1 mL | 1 mL |

The key factor to improve the electrode construction reproducibility of PVB2 was the dispersion of NaCl in the polymeric matrix composed of PVB in methanol. In this way, the composition was optimized in order to reach a suitable dispersion stable in time. For this, the amount of salts was significantly reduced fivefold whereas the polymer amount was multiplied by 1.5 in comparison to the composition of PVB1. The former, is of particular interest so that the deposition of the reference membrane cocktail could be performed by conventional methods such as drop casting, spin coating etc. . . . so that the electrode could be prepared in an automatized manner.

The selected composition of PVB2 thus affords a suitable dispersion of NaCl in the polymeric matrix, which in turn allows for an expected membrane formation on the substrate.

Example 2. Clinical Validation of the Point-of Care Device of Example 1 (Having PVC 2 and PVB2 as the Working and Reference Electrodes Respectively) for the Detection of Potassium in Blood of Patients on Hemodialysis: Comparison with a Reference Method Materials and Methods
Patients and Samples We selected 36 random patients undergoing dialysis in Hospital Clinic de Barcelona (27 men, 8 women, mean age 63±15). The underlying renal diseases were chronic glomerulonephritis in 9 patients, diabetic nephropathy in 4, polycystic kidney disease in 3, nephroangiosclerosis in 5, systemic diseases in 2, urologic disease in 3, chronic tubulo-interstitial nephritis in 3, and undiagnosed nephropathy in 6. All patients signed informed consent forms approved by the hospital's Research Committee. Whole-blood samples were collected in lithium heparin BD Vacutainer Tubes (Ref 368884).

Methods Description

ADVIA Chemistry XPT from Siemens Healthineers was used as the reference system for the potassium measurement. ADVIA Chemistry XPT performs an indirect measurement (dilution 1:33) of potassium in plasma with ion selective electrodes technology.

The point-of-care device performs a direct measurement of potassium in whole blood with ion selective electrodes technology. The POC consists of a paper-based sensor (potassium ion selective and reference electrodes) connected to a miniaturized potentiometer. The potentiometer is at the same time connected to a portable device such as a Tablet or laptop with adequate software. The paper-based sensor is disposable and requires a two point calibration before every potassium measurement. This calibration is done with two standards of 1 mM and 10 mM potassium, so that the sample will always fall inside the calibration curve. After the calibration, the sensor is rinsed with water and the whole blood sample is directly measured. The software which records the potential of the two standards and the sample can directly predict the potassium concentration.

Study Design

The study was planned in a way in which potassium values will be scattered in the whole biological range, therefore the blood was extracted from the patients before and after the dialysis session during 10 sessions. Some of the patients miss one of the sessions due to clinical or management problems. Once the blood was extracted from the patient, the analysis of the samples followed the normal procedure of the hospital: the samples were sent to the central laboratory where they were introduced in the Aptio Automation System (AAS) (Siemens Healthineers) and automatically centrifuged (2000 g for 8 minutes) to obtain the plasma. Samples were analyzed in ADVIA Chemistry XPT system with a predilution of 1:33. After the result was obtained, the samples were recovered from the ASS, homogenized again and measured with the POC in the whole blood form.

Statistics

The results of the samples were analyzed by Passing-Bablock regression and Bland-Altman plots. Passing-Bablock regression calculates a regression equation (y=ax+b) including 95% confidence intervals for the constants. Bland-Altman plot analyzes the agreement between to different methods that measure the same variable by plotting the mean of the two methods versus its difference.

Results

The ADVIA Chemistry XPT analyzer and the POC have been compared not only in terms of the conventional analytical performance parameters, but also taking into account other parameters that gain a remarkable importance when dealing with in-situ analysis, such as the time of response and the sample volume. Table 1 displays a comparison of the selected parameters for the two methodologies.

TABLE 1

Comparison of analytical and technical parameters between the two methodologies.

|  | ADVIA Chemistry XPT | POC |
| --- | --- | --- |
| Sensitivity (mV/dec) | n.r | 55.4 ± 0.3 (n = 5) |
| Limit of detection (log [K$^+$]/M) | n.r | −3.9 ± 0.1 (n = 5) |
| Linear range (mM) | 1-10 | 1-10 (n = 5) |
| Precision (mM) | 0.01-0.14 | 0.25 (n = 15) |
| Matrix | Serum/plasma heparin | Blood |
| Sample dilution | 1:33 | None |

*without sample transport; n.r. not reported

Regarding the conventional analytical parameters, no significant difference was detected between both techniques. Indeed, the linear range is the same and although sensitivity and limit of detection are not reported for the ADVIA Chemistry XPT system probably they would be very similar since the fundamental detection technique is potentiometry in both cases. However, precision is one order of magnitude higher for the reference technique. Precision is analyzed in more depth below. The parameters displayed in the second part of the table represent relevant characteristic for POC and homecare. Noteworthy, the reference technique employs diluted plasma, which involves first a centrifugation followed by a proper dilution with a buffered solution. This feature implies a much higher required sample volume for the reference method (typically of a few mL, i.e. the conventional lithium heparin tubes used in this study for collecting venous blood are of 4 mL).

Figure 1:
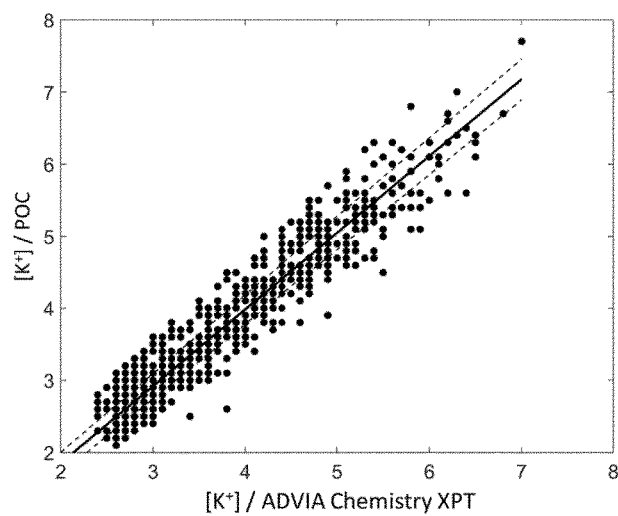
FIG. 1. Passing-Bablock regression analysis. Dashed lines represent the 95% CIs. POC=1.0769 (95% CI 1.1053/1.0455) ADVIA Chemistry XPT −0.3231 (95% CI −0.4158/−0.2205), n=694.

A total of 705 whole-blood samples were measured with the POC, and the corresponding serums with the ADVIA Chemistry XTP system. 11 of these samples were excluded from the analysis because of erroneous measurements. Passing-Bablock regression analysis was applied to the data and the results are shown in FIG. 1. The Pearson correlation coefficient ($R^2=0.953$) is high ($P<0.0001$) and Lin's concordance correlation coefficient is also substantial ($r=0.9505$), showing a strong correlation between the two methodologies.

A Bland-Altman (B&A) analysis of the data (FIG. 2A) confirms that there is no bias (0.03) between the reference technique and the POC. The 95% confidence intervals are between −0.62 and 0.68 mM. FIG. 2B shows a B&A analysis, representing the average results of the techniques versus the percentage of the difference. In FIG. 2B, at first the error appears to be higher at lower concentrations, however, this is not representative and could be attributed to the higher amount of values in the lower potassium concentrations section. We have therefore analyzed the data separately.

The invention claimed is:

1. A paper-based sensor comprising a potassium ion-selective potentiometric cell capable of selectively measuring potassium and comprising a working electrode and a reference electrode, each of the working and reference electrodes comprising paper with a conductive surface, wherein the working electrode comprises a potassium ion-selective composition prepared from a first composition comprising a first carrier solvent, between 1.6 and 2.4 mg of Valinomycin per ml of the first carrier solvent, between 0.4 and 0.6 mg of potassium Tetrakis (4-chlorophenyl) borate (KTFPB) per ml of the first carrier solvent, between 52.48 and 78.72 mg of Poly(vinylchloride) (PVC) with a molecular weight between 50000-250000 g/mol per ml of the first carrier solvent, and between 103.52 and 155.28 mg of Bis(2-ethylhexyl) sebacate) (DOS) per ml of the first carrier solvent, and wherein the reference electrode comprises a composition prepared from a second composition comprising a second carrier solvent,
   between 8 and 12 mg of sodium chloride per ml of the second carrier solvent, and between 94.88 mg and 142.32 mg of Butvar B-98 per ml of the second carrier solvent,
   wherein Butvar B-98 is polyvinyl butyral having a molecular weight between 40000-70000 g/mol with a butyral content between 78 and 80% weight per total weight of the polyvinyl butyral (w/w), a hydroxyl content between 18 and 20% (w/w) and an acetate content less than 2.5%.

2. The paper-based sensor of claim 1, wherein the first composition comprises or consists of the first carrier solvent, between 1.8 and 2.2 mg of Valinomycin per ml of the first carrier solvent, between 0.45 and 0.55 mg of potassium Tetrakis (4-chlorophenyl) borate (KTFPB) per ml of the first carrier solvent, between 59.04 and 72.16 mg of Poly(vinylchloride) (PVC) per ml of the first carrier solvent, and between 116.46 and 142.34 mg of Bis(2-ethylhexyl) sebacate (DOS) per ml of the first carrier solvent.

3. The paper-based sensor of claim 2, wherein the first composition consists of the first carrier solvent, between 1.8 and 2.2 mg of Valinomycin per ml of the first carrier solvent, between 0.45 and 0.55 mg of potassium Tetrakis (4-chlorophenyl) borate (KTFPB) per ml of the first carrier solvent, between 59.04 and 72.16 mg of Poly(vinylchloride) (PVC) per ml of the first carrier solvent, and between 116.46 and 142.34 mg of Bis(2-ethylhexyl) sebacate (DOS) per ml of the first carrier solvent.

4. The paper-based sensor of claim 1, wherein the second composition comprises the second carrier solvent, between 9 and 11 mg of sodium chloride per ml of the second carrier solvent, and between 106.74 mg and 130.46 mg of Butvar B-98 per ml of the second carrier solvent.

5. A method for determining the concentration of potassium in an aqueous solution, comprising bringing a portion of the aqueous solution into contact with the paper-based sensor of claim 1, and measuring a difference in potential between the portion of the aqueous solution and the reference electrode, wherein said aqueous solution is a biological fluid selected from undiluted whole blood, cerebrospinal fluid, intracellular fluids, saliva, blood sera, blood plasma, sweat and urine.

6. The paper-based sensor of claim 1, wherein the conductive surface of the reference electrode comprises carbon, silver, Zinc or gold.

7. The paper-based sensor of claim 1, wherein the conductive surface of the working electrode comprises Ag/AgCl.

8. The paper-based sensor of claim 1, wherein the first carrier solvent comprises tetrahydrofuran.

9. The paper-based sensor of claim 1, wherein the second carrier solvent comprises methanol.

10. The paper-based sensor of claim 1, wherein the first composition consists of the first carrier solvent, between 1.6 and 2.4 mg of Valinomycin per ml of the first carrier solvent, between 0.4 and 0.6 mg of potassium Tetrakis (4-chlorophenyl) borate (KTFPB) per ml of the first carrier solvent, between 52.48 and 78.72 mg of Poly(vinylchloride) (PVC) with a molecular weight between 50000-250000 g/mol per ml of the first carrier solvent, and between 103.52 and 155.28 mg of Bis(2-ethylhexyl) sebacate (DOS) per ml of the first carrier solvent.

\* \* \* \* \*